(12) United States Patent
Haley et al.

(10) Patent No.: US 8,346,370 B2
(45) Date of Patent: Jan. 1, 2013

(54) DELIVERED ENERGY GENERATOR FOR MICROWAVE ABLATION

(75) Inventors: Kaylen J. Haley, Westminster, CO (US); Kyle R. Rick, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 889 days.

(21) Appl. No.: 12/241,861

(22) Filed: Sep. 30, 2008

(65) Prior Publication Data

US 2010/0082022 A1    Apr. 1, 2010

(51) Int. Cl.
    *A61F 2/00* (2006.01)
(52) U.S. Cl. ............... 607/101; 324/600; 606/38
(58) Field of Classification Search ........... 606/38, 606/42, 33; 324/600; 343/703; 600/430; 607/101–102, 154–156; 333/17.1, 101
See application file for complete search history.

(56) References Cited

U.S. PATENT DOCUMENTS

| | | | |
|---|---|---|---|
| 3,998,538 A | 12/1976 | Urso | |
| 4,204,549 A | 5/1980 | Paglione | |
| 4,228,809 A | 10/1980 | Paglione | |
| 4,247,815 A | 1/1981 | Larsen | |
| 4,311,154 A | 1/1982 | Sterzer et al. | |
| 4,741,348 A | 5/1988 | Kikuchi | |
| 4,744,372 A | 5/1988 | Kikuchi | |
| 5,097,846 A | 3/1992 | Larsen | |
| 5,354,325 A * | 10/1994 | Chive et al. | 607/101 |
| 5,364,392 A | 11/1994 | Warner et al. | |
| 5,405,346 A | 4/1995 | Grundy et al. | |
| 5,562,720 A | 10/1996 | Stern et al. | |
| 5,651,780 A | 7/1997 | Jackson | |
| 5,683,382 A | 11/1997 | Lenihan et al. | |
| 5,865,788 A | 2/1999 | Edwards et al. | |
| 5,904,709 A | 5/1999 | Arndt et al. | |
| 5,931,836 A * | 8/1999 | Hatta et al. | 606/38 |
| 5,957,969 A | 9/1999 | Warner et al. | |
| 5,961,871 A | 10/1999 | Bible et al. | |
| 5,983,141 A | 11/1999 | Sluijter et al. | |
| 6,016,452 A | 1/2000 | Kasevich | |
| 6,067,475 A | 5/2000 | Graves et al. | |
| 6,097,985 A | 8/2000 | Kasevich et al. | |
| 6,134,476 A | 10/2000 | Arndt et al. | |
| 6,165,173 A | 12/2000 | Kamdar | |
| 6,175,768 B1 | 1/2001 | Arndt et al. | |
| 6,181,970 B1 | 1/2001 | Kasevich | |
| 6,216,704 B1 | 4/2001 | Ingle et al. | |
| 6,233,490 B1 | 5/2001 | Kasevich | |
| 6,246,912 B1 | 6/2001 | Sluijter et al. | |
| 6,273,886 B1 | 8/2001 | Edwards et al. | |

(Continued)

FOREIGN PATENT DOCUMENTS

DE       3942998       0/1991

(Continued)

OTHER PUBLICATIONS

International Search Report EP 09012389 dated Jun. 7, 2010.

(Continued)

*Primary Examiner* — Kevin C Sirmons
*Assistant Examiner* — Deanna K Hall

(57) ABSTRACT

A microwave system for generating microwave energy to tissue according to an energy control algorithm is disclosed. The system includes a microwave generator configured to select an energy control algorithm, programmed in the microwave generator that corresponds to a microwave energy delivery device connected to the generator.

6 Claims, 5 Drawing Sheets

U.S. PATENT DOCUMENTS

| | | | |
|---|---|---|---|
| 6,358,245 | B1 | 3/2002 | Edwards et al. |
| 6,471,696 | B1 | 10/2002 | Berube et al. |
| 6,485,486 | B1 | 11/2002 | Trembly et al. |
| 6,699,241 | B2 | 3/2004 | Rappaport et al. |
| 6,743,225 | B2 | 6/2004 | Sanchez et al. |
| 6,784,405 | B2 | 8/2004 | Flugstad et al. |
| 6,847,848 | B2 | 1/2005 | Sterzer et al. |
| 7,226,446 | B1 | 6/2007 | Mody et al. |
| 7,344,533 | B2 | 3/2008 | Pearson et al. |
| 7,393,352 | B2 | 7/2008 | Berube |
| 7,419,487 | B2 | 9/2008 | Johnson et al. |
| 2002/0087151 | A1 | 7/2002 | Mody et al. |
| 2003/0153908 | A1 | 8/2003 | Goble et al. |
| 2004/0133189 | A1 | 7/2004 | Sakurai |
| 2004/0243120 | A1 | 12/2004 | Orszulak |
| 2005/0033278 | A1 | 2/2005 | McClurken et al. |
| 2006/0055591 | A1 | 3/2006 | Eriksson |
| 2006/0079774 | A1 | 4/2006 | Anderson |
| 2006/0155270 | A1 | 7/2006 | Hancock et al. |
| 2006/0191926 | A1* | 8/2006 | Ray et al. ............... 219/759 |
| 2006/0224152 | A1 | 10/2006 | Behnke et al. |
| 2007/0203480 | A1 | 8/2007 | Mody et al. |
| 2007/0233057 | A1 | 10/2007 | Konishi |
| 2007/0282319 | A1 | 12/2007 | Van Der Weide et al. |
| 2009/0018536 | A1 | 1/2009 | Behnke |
| 2010/0082085 | A1 | 4/2010 | Pai et al. |
| 2010/0168730 | A1 | 7/2010 | Hancock et al. |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 4339049 | 5/1995 |
| DE | 19717411 | 11/1998 |
| DE | 19848540 | 5/2000 |
| EP | 246350 | 11/1987 |
| EP | 0296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1186274 | 4/2006 |
| EP | 880220 | 6/2006 |
| EP | 1810630 | 7/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| GB | 2434872 | 8/2007 |
| SU | 166452 | 1/1965 |
| SU | 727201 | 4/1980 |
| WO | WO 9207622 | 5/1992 |
| WO | WO 2004047659 | 6/2004 |
| WO | WO2005115235 | 12/2005 |
| WO | W02006/105121 | 10/2006 |
| WO | WO2007055491 | 5/2007 |
| WO | WO 2007055491 | 5/2007 |
| WO | WO 2007105963 | 9/2007 |
| WO | WO2008/043999 | 4/2008 |
| WO | WO2008043999 | 4/2008 |
| WO | WO2008044000 | 4/2008 |
| WO | WO2008044013 | 4/2008 |
| WO | WO 2008044013 | 4/2008 |
| WO | WO 2008071914 | 6/2008 |
| WO | WO2008/110756 | 9/2008 |
| WO | WO 2008110756 | 9/2008 |

OTHER PUBLICATIONS

U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, " A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report EP 09012388.6 dated Apr. 13, 2010.
International Search Report EP 09012391.0 dated Apr. 19, 2010.
International Search Report EP09012392 dated Mar. 30, 2010.
International Search Report EP09012386 dated Apr. 1, 2010.
International Search Report EP09012396 dated Apr. 7, 2010.
International Search Report EP09012400 dated Apr. 7, 2010.

* cited by examiner

DELIVERED ENERGY GENERATOR FOR MICROWAVE ABLATION

BACKGROUND

1. Technical Field

The present invention relates to systems and methods for performing a medical procedure, wherein the medical procedure includes the generation and transfer of energy from an energy source to a dynamically changing device and, more particularly, efficient transfer of energy through a microwave energy delivery, measurement and control system.

2. Description of Related Art

During microwave ablation procedures, the electrical performance of a microwave antenna probe changes throughout the course of an ablation treatment. The change in performance may be due to the device or due to changes in tissue properties. The ability to observe parameters indicative of the operation of the microwave energy delivery device and parameters indicative of energy delivered to tissue provides a better understand of individual properties of microwave energy delivery devices and the effect these properties have on energy delivery.

The present disclosure describes the use of a Microwave Research Tool (MRT) to conduct extensive testing of various microwave energy delivery devices. Various tools, control algorithms and data collection algorithms were used to vary the delivery of microwave energy and to monitor the effectiveness of the ablation devices and the ablation size in tissue. Testing included delivery of microwave energy as a continuous wave and as a pulsed wave over a fixed time at varying energy levels and with several different microwave energy delivery devices. Tissue temperature was monitored with temperature sensors inserted into tissue, energy delivery was monitored by the MRT and various parameters related to energy delivery were calculated after each test.

Estimation and/or measurements of ablation size and energy delivery were used to compare the performance and operation of various microwave energy delivery devices to gain a better understand ablation and the understanding of the device performance and the effect the performance had on ablation. This new understanding was applied in the present disclosure in a microwave generator with device specific microwave energy control algorithms.

SUMMARY

The present disclosure relates to a microwave energy delivery and control system for use in performing a medical procedure. In one embodiment, the microwave system generates microwave energy according to an energy control algorithm and provides microwave energy to tissue. The system includes a microwave generator configured to select an energy control algorithm (programmed in the microwave generator) that corresponds to a microwave energy delivery device connected to the microwave generator.

In one embodiment, the microwave system includes a microwave energy delivery device identification module configured to identify the microwave energy delivery device connected to the microwave generator. The microwave energy delivery device identification module may be configured to actively identify the microwave energy delivery device by identifying a microwave energy delivery device resistor circuit, a bar code, an Aztec code, an RFID tag, memory containing device identification information and a physical characteristic of the microwave energy delivery device.

The microwave energy delivery device identification module may also be configured to passively identify the microwave energy delivery device by identifying an impedance characteristic, a product specific characteristic or a characteristic related energy delivery, such as, for example, forward energy or reflected energy.

In another embodiment the microwave system may include an energy control algorithm selection module to select an energy control algorithm that corresponds to the connected microwave energy delivery device.

In yet another embodiment, the microwave system includes an energy control algorithm selection module configured to receive data related to the identified microwave energy delivery device from a microwave energy delivery device identification module. The energy control algorithm selection module may select an energy control algorithm that corresponds to an identified microwave energy delivery device.

A method of delivering microwave energy is also disclosed and includes the steps of: delivering energy to a microwave energy delivery device; measuring at least one parameter related to the energy delivery; identifying the microwave energy delivery device from the at least one parameter; selecting an energy algorithm that corresponds to the identified microwave energy delivery device; and using the selected algorithm to deliver microwave energy to tissue.

Yet another method of the present disclosure includes the steps of: delivering energy to a microwave energy delivery device; measuring at least one parameter related to the energy delivery; identifying the microwave energy delivery device from the at least one parameter; selecting an energy algorithm that corresponds to the identified microwave energy delivery device; and using the selected algorithm to deliver microwave energy to tissue. The parameter may be an impedance parameter or energy parameter, such as, for example, forward energy or reflected energy.

Yet another method of the present disclosure includes the steps of: delivering a first pulse of microwave energy to a microwave energy delivery device; measuring at least one parameter related to the first pulse of energy delivery; identifying the microwave energy delivery device from the at least one parameter; selecting an energy algorithm that corresponds to the identified device; and delivering subsequent pulses of microwave energy using the selected energy algorithm to deliver microwave energy to tissue. The parameter may be an impedance parameter or an energy parameter, such as, for example, forward energy or reflected energy.

Yet another method of the present disclosure includes the steps of: including an identification characteristic in a microwave energy delivery device; identifying the identification characteristic; selecting an energy algorithm that corresponds to the identified identification characteristic; and using the selected energy algorithm to deliver microwave energy to tissue. The identification characteristic may be a resistor circuit, a bar code, an Aztec code, an RFID tag, memory containing device identification information or a physical characteristic of the microwave energy delivery device.

DETAILED DESCRIPTION

Detailed embodiments of the present disclosure are described herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present disclosure incorporates an indicator on the microwave generator indicative of delivered energy, such as, for example, a calculation of delivered energy. To calculate delivered energy the microwave generator tracks forward power set by the user as well as any reflected power returning to the generator due to a mismatch between the antenna and the generator. Based on the two power measurements, energy delivered to the tissue can be estimated and displayed for the user. Based on testing, it was discovered that ablation size is related to the amount of energy deposited to tissue more so that the specific method of energy delivery (i.e., continuous energy delivery verses a pulsed energy signal). As such, the indicator of delivered energy provides a robust measure for various ablation scenarios.

Testing observations also revealed an unexpected discovery related to delivered energy and overall antenna design. It was discovered that differences exist between the amounts of energy delivered to the tissue for a given microwave ablation device. The discrepancies are driven by differences in overall antenna design and/or function as well as the precision of the energy calculation and measurement tool used to track energy disposition into tissue. As such, a microwave generator incorporated with the ability to perform one or more of the various measurements disclosed herein (passively or actively) may determine the specific device connected with the microwave generator. As a result thereof, the microwave generator may select a specific algorithm to provide a more accurate energy calculation.

Figure 1:
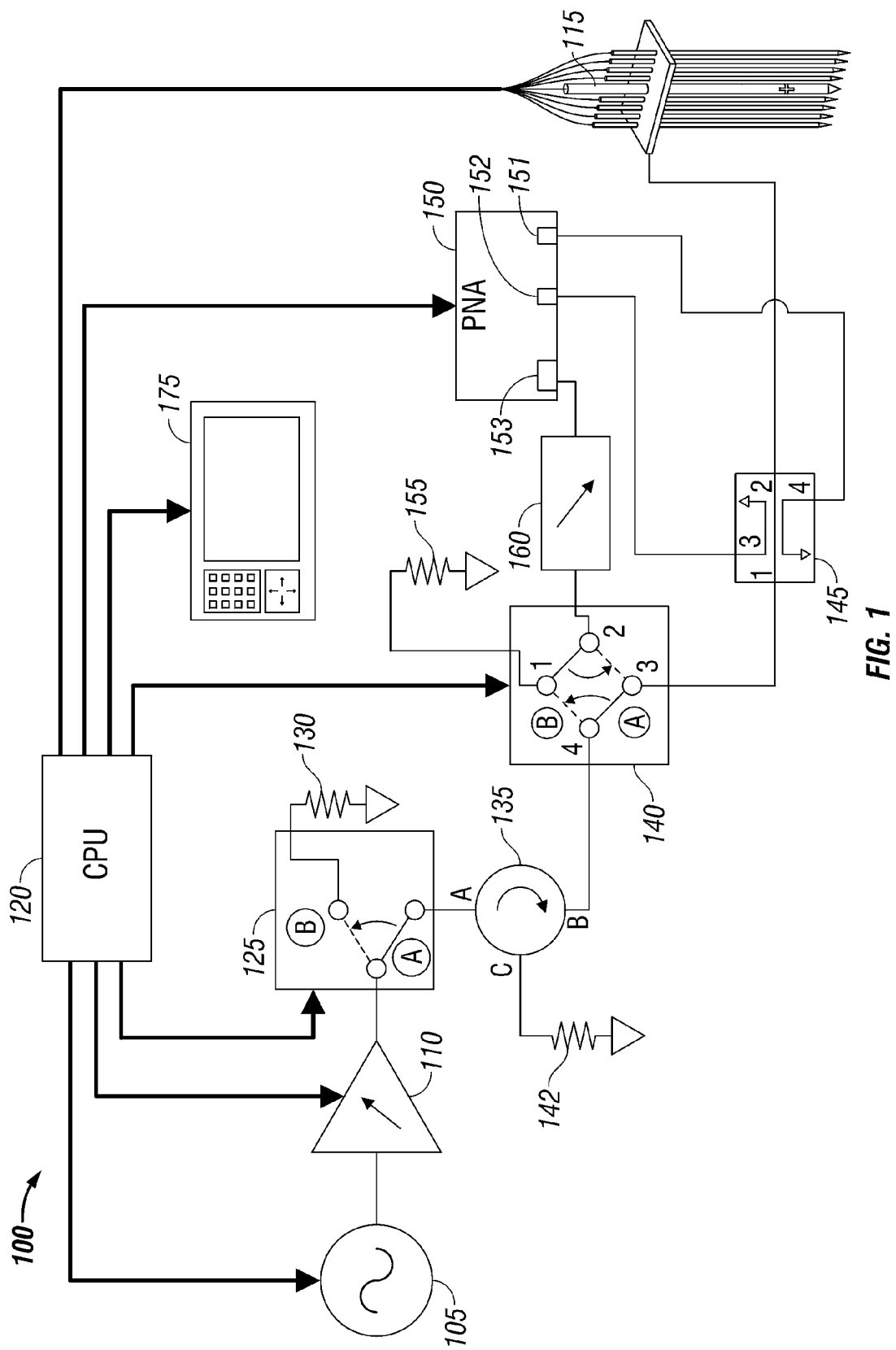
FIG. 1 is a functional block diagram of a microwave energy delivery, measurement and control system used to conduct testing of microwave energy delivery devices in accordance with embodiments of the present disclosure.

Referring to FIG. 1, a Microwave Research Tool (MRT), including a measurement and control system, for use in performing a medical procedure or medical procedure testing and employing embodiments of the present disclosure, is generally designated as 100. MRT 100 may include the functionality of a microwave generator typically used to deliver microwave energy or with improved functionality as described in U.S. patent application Ser. No. 12/242,102, titled "Microwave Ablation Generator Control System", filed concurrently with the present disclosure and herein incorporated by reference. MRT 100 includes individual components, as illustrated in FIG. 1, or the functionality of individual components may be combined or included in one or more components. Components are interconnected with suitable cables and/or connectors. In the present disclosure, a Microwave Research Tool 100 (hereinafter "MRT") is used to perform tests with several different types of microwave energy delivery devices. Device specific performance data is collected by the MRT, analyzed, compared and used to determine product specific parameters and algorithms for use in a microwave generator.

A MRT was used to conduct the testing described hereinbelow and to discover and formulate the device specific algorithms. The MRT is described below in detail followed by a description of an ablation testing assembly, testing results and a microwave generator with device specific control algorithms.

Microwave Research Tool

The MRT includes a microwave energy delivery system, a measurement system and a supervisory control system. Each system is described individually although each system may share common components as will be discussed hereinbelow.

The microwave energy delivery system includes a signal generator 105 capable of generating and supplying a high frequency microwave signal to an amplifier 110. Signal generator 105 may be a single frequency generator or may include variable frequency capability. Signal generator 105 may also be capable of providing a signal including two or more frequencies wherein the ablation device 115 under test resonates at two or more frequencies. Supervisory control system, e.g., CPU 120 may control various aspects of the signal generator 105 such as, for example, the signal delivery timing, the frequency (or frequencies) of the output and the phase of the signal.

Amplifier 110 receives and amplifies the signal from the signal generator 105 to a desirable energy level. Amplifier 110 may be a single or multi-stage amplifier 110 and may include one or more signal conditioning circuits or filters such as, for example, a low, high or bandpass circuits. Amplifier 110 gain may be fixed or controlled by a suitable controller, such as, for example, a control algorithm in the CPU 120 or by manual adjustment (not shown).

Amplifier 110 supplies a continuous, amplified microwave signal to a hot switch relay 125. Hot switch relay 125 is controlled by the CPU 120 and switches the amplified microwave signal to one of an amplifier burn-off load resistor 130 and a circulator 135. The hot switch relay 125 in Position A delivers energy to the ablation device 115 through the circulator 135 and directional coupler 145. The hot switch relay 125 in Position B delivers energy away from the ablation device 115 and into an amplifier burn-off load resistor 130.

Hot switch relay 125 may be any suitable solid-state high power switch capable of switching a high power microwave energy signal. Hot switch relay 125 receives the high power microwave energy signal from the signal generator 105 and amplifier 110 and passes the signal between one of the amplifier burn-off load resistor 130 or the circulator 135 without powering down the signal generator 105 or amplifier 110. One suitable device is a 150 watt 915 MHz dual pole single-throw solid-state switch that can be powered by two DC supply lines and controlled with a single TTL signal line from the CPU 120. In use, the hot switch relay 125 allows the MRT 100 to provide near instantaneous power, without creating amplifier transients, by eliminating the need to power down the signal generator 105 or amplifier 110.

Continuous operation of the signal generator 105 and amplifier 110 is desirable to prevent the introduction of amplifier transients into the microwave energy delivery system often created during power-up. To maintain continuous operation the switching time between Positions A and B on the hot switch relay 125 should be sufficiently fast to allow continuous operation of the signal generator 105 and amplifier 110. For example, at 915 MHz hot switch relay may switch from Position A to Position B in about 360 ns and from Positions A to Position B in about 370 ns.

Amplifier burn-off load resistor 130 may be any suitable coaxial terminator capable of dissipating microwave energy while generating a minimal amount of VSWR, or reflective energy, over the bandwidth of the signal generator 105. One such device is a 1433-3 50-ohm 250-watt coaxial terminator sold by Aeroflex/Weinschel of Plainview N.Y. and intended for operation over the bandwidth of DC to 5 GHz. Over the entire bandwidth of the amplifier burn-off load resistor 130 the VSWR may be less than 1.1.

Circulator 135 is a passive three port device that eliminates standing waves between the hot switch relay 125 and the transfer switch 140. Circulator 135 passes signals received on Port A to Port B, signals received on Port B to Port C and signals received on Port C to Port A. When hot switch relay 125 is in Position A, the microwave energy signal is passed from Port A of the circulator 135 to the transfer switch 140 connected to Port B. Reflected energy from the transfer switch 140 or the ablation device 115, received on Port B, is passed to Port C and dissipated through the reflected energy burn-off load resistor 142. Reflected energy burn-off load resistor 142 is similar in function to the amplifier burn-off load resistor 130 as discussed hereinabove.

Hot switch relay 125 and transfer switch 140, when switching from Positions A to Positions B, appears as open circuits to the circulator 135. During and after switching occurs, the circulator 135 clears the system of any residual power left in the system by directing the residual power into the reflected energy burn-off load resistor 142.

In addition, when hot switch relay 125 switches from Position A to Position B energy from dual directional coupler 145 and the ablation device 115 is directed through the transfer switch 140, to the circulator 135 and is dissipated by the reflected energy burn-off load resistor 142. With the hot switch relay 125 and the transfer switch 140 both in Position B the MRT 100 connects to the ablation device 115 and performs active measurements thereof.

Transfer switch 140 provides sufficient isolation between the measurement system and the microwave energy delivery system. In Position A, the high power microwave energy signal is received on Port 4, passed to Port 3 and to the directional coupler 145. The precision network analyzer 150, connected to Port 2 of the transfer switch 140, connects to the transfer switch load resistor 155 on Port 1. In Position B, energy received on Port 4 is passed to Port 1 and dissipated by the transfer switch load resistor 155, and the precision network analyzer 150 on Port 2 is connected through Port 3 to the directional coupler 145 and the ablation device 115. The transfer switch 140 maintains isolation between Ports 4 and 2 (and isolation between the high power microwave energy and the precision network analyzer) regardless of the position of the transfer switch 140 position.

In operation, microwave energy is switched to the amplifier burn-off load resistor 130 by the hot switch relay 125 before the transfer switch 140 switches from Position A to Position B. As such, the transfer switch 140 does not operate as a "hot switch" because it is not under a load from the signal generator 105 or amplifier 110 when switching occurs.

One suitable device that may be used as a transfer switch 140 is a coaxial transfer switch sold by Ducommun of Carson, Calif. The transfer switch 140 may operate with less than 1.05 VSWR, better than 0.1 dB insertion loss and less than 80 dB isolation for all states at 915 MHz. The hot switch relay 125 switches out the high energy microwave energy signal before the transfer switch 140 transitions, therefore, transition times for the transfer switch 140 are not critical. High-to-low transition times for the transfer switch 140 may be about 75 ms and low-to-high transitions times may be about 25 ms.

Directional coupler 145 may be configured to operate like most conventional directional couplers known in the available art. As illustrated in FIG. 1, directional coupler 145 passes the high power microwave energy signal received on Port 1 to Port 2 with minimal insertion loss. Energy reflected back from the ablation device 115 and received on Port 2 of the directional coupler 145 is passed through the transfer switch 140 to Port B of the circulator 135. Energy received from the transfer switch 140 on Port B of the circulator 135 is passed to Port C of the circulator 135 and dissipated by the reflected energy burn-off load resistor 142.

Directional coupler 145 samples a small portion of each of the signals received on Port 1 and Port 2 and passes a small portion of the signals to Ports 3 and 4, respectively. The signals on Port 3 and 4 are proportional to the forward and reverse power, respectively. The measurement system measures the signal samples and provides the measurements to the CPU 120. The forward and reverse power measurements from the directional coupler 145 are passively measured and the samples may be taken continuously or at a periodic sample frequency. Unlike the broadband scattering parameter measurements, the directional coupler 145 measurements are indirect measurements of the delivered energy. As such, the measurements from the directional coupler 145 are limited to the bandwidth of the microwave energy supplied to the ablation device 115 from the signal generator 100 (i.e., feedback is fixed to the frequency of the high power microwave energy signal).

One suitable directional coupler 145 is sold by Werlatone of Brewster, N.Y. The directional coupler 145 may be a 40 dB dual directional coupler with 30 dB directivity and less than 0.1 dB insertion loss from 800 MHz to 3 GHz.

CPU 120 is capable of executing instructions and/or performing algorithms and configured to receive one or more inputs and may be configured to control one or more devices in the MRT 100. Inputs may include analog inputs, such as, for example, signals from the forward and reverse coupling ports, Port 3 and Port 4 of the directional coupler 145, respectively. Inputs may also include digital inputs, such as, for example, communication with one or more devices (i.e., precision network analyzer 150).

A suitable MRT 100 CPU 120 may be housed in a PXI System (PCI eXtensions for Instrumentation includes) sold by National Instrument of Austin, Tex. The PXI includes a chassis that may connect various functional components over a PCI backplane, across a PCI bridge or by any other suitable connection. The PXI may include a system controller and various other modules in additional slots such as, for example, a system timing module, an input module, and output module and a network analyzer in slots and configured to communicate therebetween. PXI, or module contained therewithin, may interface and/or control at least one of the measurement equipment, switch control, data processing, algorithm implementation, tuning network control, microwave source control (frequency and/or power) and a user interface.

User interface 175 is used for monitoring and controlling the MRT 100. Control system or operational parameters may be monitored, adjusted, tracked, sampled and/or logged via the user interface 175. For example, a software package such as programs known by their trademarks LABVIEW® or WONDERWARE® may be programmed to control, monitor and/or log the various aspects of the MRT.

In the present embodiment, a virtual instrument (VI) was created in the user interface 175 to control the PXI, instrument settings and to collect data. Control through the VI may include total ablation time, power meter offsets, network analyzer configuration and calibration, output duty cycle and amplifier output power. Data collected, monitored or logged by the VI may include ablation time, temperature measurements, outputs (magnitude and/or phase), forward and reflected power, broadband scatter parameter measurements and delivered power to tissue.

CPU 120 may enable or disable the signal generator 105 or may provide at least one reference signal to the signal generator 105, such as, for example, the frequency or gain of the microwave signal. CPU 120 may provides a reference signal to the amplifier 110 related to the desired gain, may control the position of at least one of the hot switch relay 125 and the transfer switch 140 and may provide control signals to the precision network analyzer 150.

CPU 120, or precision network analyzer 150, may include the functionality of both the supervisory control system and measurement system or any combination thereof. For example, the precision network analyzer receives the passive inputs and performs the active measurements. Precision network analyzer 150 may be any suitable network analyzer capable of performing measurements of the DUT 115 and/or determining loss information for transmission system. Precision network analyzer 150 may connect to the transfer switch 140 through an attenuator 160 or other suitable protection device. Attenuator 160 may scale the signal from the transfer switch 140 to one of a suitable power, current and voltage level.

Attenuator 160 may be a limiting device, such as, for example, a fuse-type device that opens a circuit when a high power signal is detected. Limiting device may appear transparent to the precision network analyzer 150 until the limiting device is hit with a high power signal. One such device is a power limiter sold by Agilent of Santa Clara, Calif. is configured to provide a 10 MHz to 18 GHz broadband precision network analyzer input protection from excess power, DC transients and electrostatic discharge. The attenuator 160 limits RF and microwave power to 25 dBm and DC voltage to 30 volts at 25° C. at 16 volts at 85° C. with turn-on times of less than 100 picoseconds.

Limiting device may function as either a fuse-type device or a circuit breaker type device. Fuse-type device may need to be replaced after a failure while a circuit-breaker type device may include an electrical or mechanical reset to reinitialize and reset the circuit breaker after a failure. MRT 100 may include reset functionality that is initiated and/or performed by the CPU 120 or the like.

In an energy delivery mode, as illustrated in FIG. 1, the MRT 100 is configured to delivery energy to the ablation device 115. The microwave energy signal from the signal generator 105 and amplifier 110 is passed through the hot switch relay 125 in Position A, through the circulator 135 and the transfer switch 140 (in Position A), through the directional coupler 145 and to the ablation device 115. The measurement system (i.e., the CPU 120 or precision network analyzer 150) passively measures forward and reflected energy at Port 3 and 4 of the dual directional coupler 145. The precision network analyzer 150 is isolated from the high energy microwave signal by the transfer switch 140.

Figure 2:
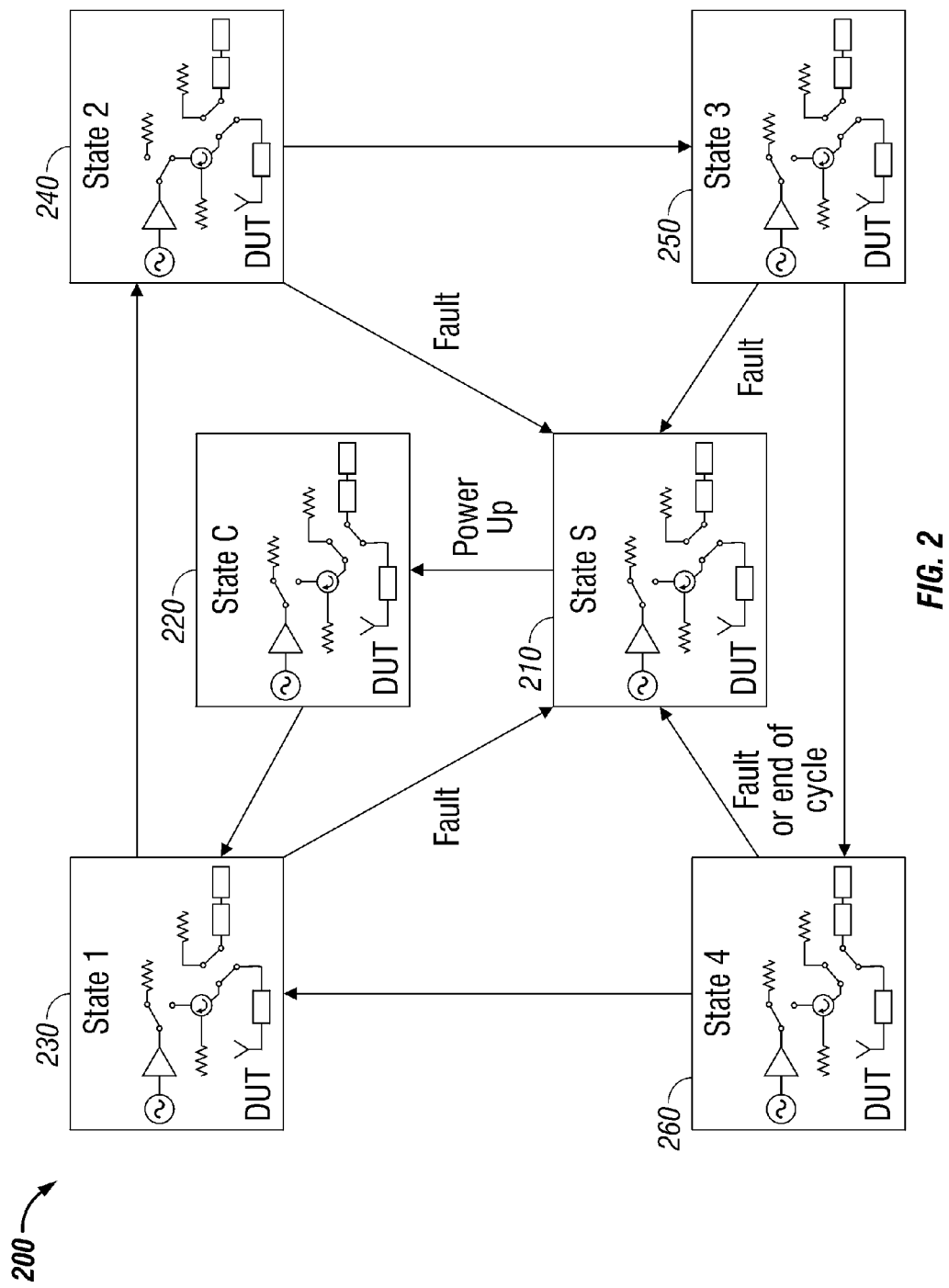
FIG. 2 is a state machine, functional block diagram of the microwave energy delivery, measurement and control system of FIG. 1.

FIG. 2 displayed the MRT system state machine 200. The six states, defined as State S, State C and States 1-4, show the various states of the MRT 100 in FIG. 1 and are designated as 210-260, respectively. Operation of the MRT 100 of FIG. 1 is determined by the position of the two switches, the hot switch relay 125 and the transfer switch 140, and the operation of the MRT 100 flows between the six states. Multiple states end in the same switch orientation but are shown as different states to illustrate a unique control sequence. The utility of each state during the ablation cycle are described hereinbelow.

State S 210 is the standby state of the MRT. Both switches in State S 210 default to this configuration and the MRT 100 is therefore in a failsafe position, (i.e., the default condition when power is removed or on power failure directs energy away from the patient or medical personnel). As such, the system provides for safe operation in the case of power failure, fault detection or when the system is not in use. A failsafe standby state also ensures that on startup, transient power spikes or other potentially dangerous power surges from the amplifier 110 are directed into the amp burn-off load resistor 130 thereby protecting equipment downstream from the hot switch relay 125.

State C 220 is the Calibration State 220 of the MRT. During the Calibration State 220 the hot switch relay 125 directs microwave power from the signal generator 105 and amplifier 110 to the amp burn-off load resistor 130 and the transfer switch 140 connects the precision network analyzer 150 to the ablation device 115. One or more calibrations are performed during this state. In one calibration the precision network analyzer 150 is calibrated to the ablation device 115 reference plane, through the attenuator 160, transfer switch 140 and directional coupler 145, for broadband scattering parameter measurements. A second calibration involves measurement of attenuation of the line between the directional coupler 145 output port and the ablation device 115 reference plane. This attenuation is used to calibrate power measurements at the directional coupler 145 to power delivered to the ablation device 115. An initial broadband scattering parameter measurement may be made during the Calibration State 220 to capture the ablation device 115 impedance within uncooked tissue.

State 1 130 begins post calibration and after State 4 260. During State 1 130, the transfer switch 140 is activated which connects the ablation device 115 load to Port 2 of the circulator 140 and the precision network analyzer 150 to the terminal switch load resistor 155. In State 1 230, the only high power signal present in the system is flowing between the signal generator 105, the amplifier 110, hot switch relay 125 in Position B and the amplifier burn-off resistor 130. State 1 230 may include a delay to ensure that the transfer switch 140 has transitioned from Position B to Position A. A fault condition in State 1 230 returns the system to State S 210, the standby state.

State 2 240 begins after the transfer switch 140 has completed the transfer switch's 140 switching cycle in State 1 230. A high control signal is delivered to the hot switch relay 125 from the CPU 120 that directs power from the signal generator 105 and amplifier 110 through the circulator 135, transfer switch 140, directional coupler 145 and into the ablation device 115. State 2 240 is the period during which an ablation is generated and generally represents the majority of system time. A fault condition in State 2 240 returns the system to State S 210, the standby state.

State 3 250 ends a period of power delivery to the ablation device 115 in preparation for a precision network analyzer 150 scattering parameter measurement. A low signal is presented to the hot switch relay 125 directing power from the signal generator 105 and amplifier 110 into the amplifier burn-off load resistor 130. A period of clear line wait time is added to the end of state 3 to allow the system to clear the lines of high power signals. A fault condition in State 3 returns the system to State S, the standby state.

State 4 260 is initiated after the clear line wait time at the end of State 3 250 expires. State 4 260 is initiated by activating the transfer switch 140. Activation of the transfer switch 140 restores the system to the calibration configuration allowing the precision network analyzer to perform broadband scatter parameter measurement of the ablation device 115. The only high power signals present in the system flow from the amplifier 105 through the hot switch relay 125 and into the amplifier burn-off load resistor 130. After the precision network analyzer 150 completes a measurement cycle the system leaves State 4 260 and re-enters State 1 230 and the MRT 100 repeats the cycle unless the ablation cycle has ended or a fault occurs, in which case the system enters State S 210 the standby state.

The MRT system state machine 200 essentially eliminates the risk of high power signals from potentially damaging sensitive microwave equipment, such as, for example, the precision network analyzer 150. Additional switching and clear line delay times may be added into the system to ensure the safety aspects of the system architecture.

Ablation Testing Assembly

Figure 3:
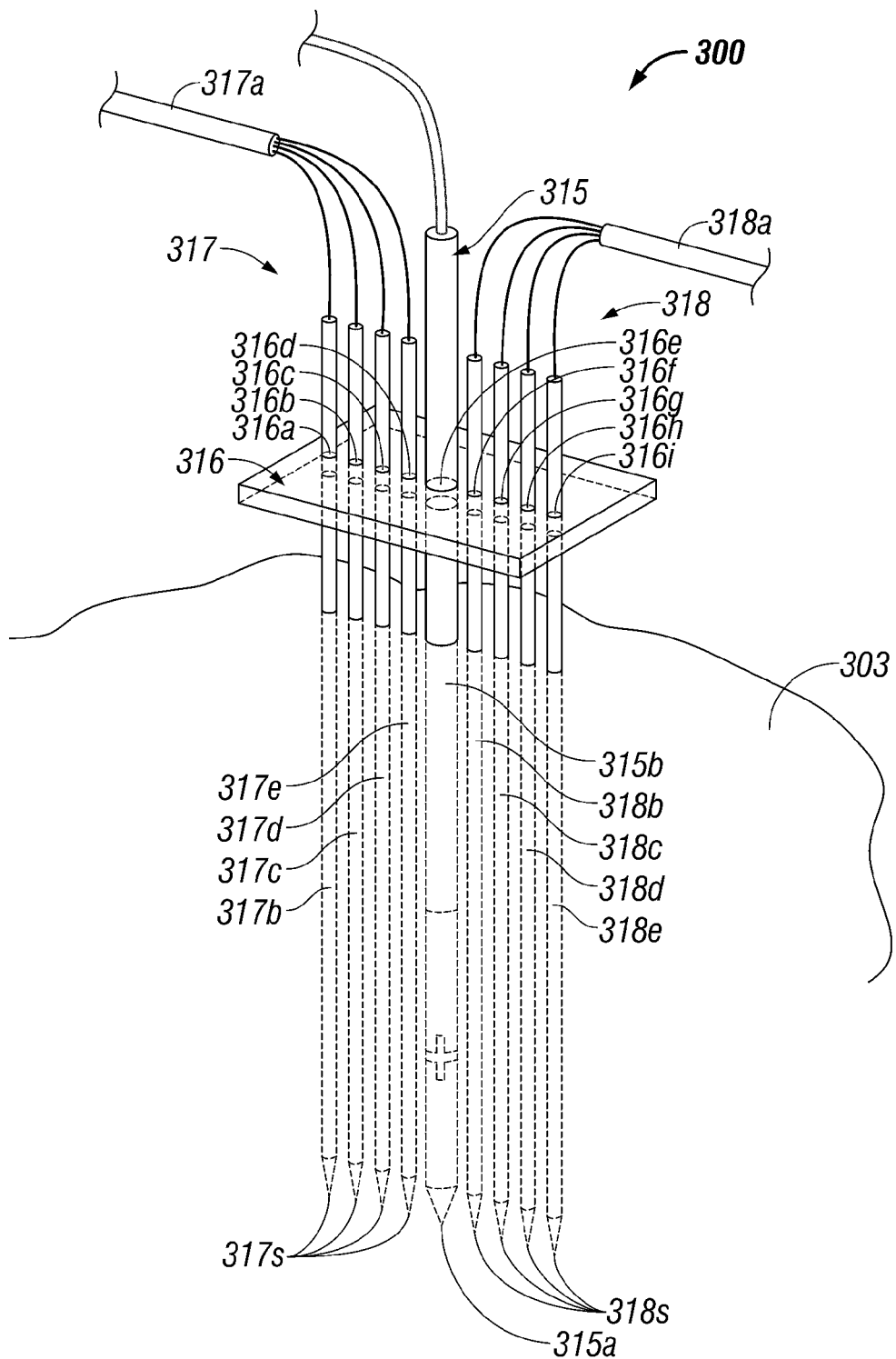
FIG. 3 is an illustration of an ablation testing assembly used in accordance with the testing of the present disclosure to position a microwave energy delivery device and at least one temperature sensor assembly in tissue.

FIG. 3 is an illustration of an ablation testing assembly 300 used to position the microwave energy delivery device 315 into tissue 303. The testing assembly 300 includes a fixture 316, a microwave energy delivery device 315 and at least one temperature sensor assembly 317, 318. An MRT equivalent to the MRT 100 described in FIG. 1 was used to perform ablation tests with on various microwave energy delivery devices and to record data from each test.

Fixture 316 forms a plurality of inserts 316*a-i* adapted to receive devices 315, 317*b-e*, 318*b-e* therethrough. A microwave energy delivery device 315 is positioned in the center insert 316*e*. Temperature probes 317*b-e*, 318*b-e* of the temperature sensor assemblies 317, 318, respectively, are positioned adjacent the microwave energy delivery device 315. Inserts 316*a-i* are spaced from each other and from the microwave energy delivery device 315 to provide separation between sensors 317*s*, 318*s* and between the sensors 317*s*, 318*s* and the microwave energy delivery device 315. For example, spacing between the inserts 316*a-i* (and the probes 317*b-e*, 318*b-e* inserted therethrough) provides spacing of the temperature sensors 317*s*, 318*s* positioned at the distal ends of each probe 317*b-e*, 318*b-e*.

Fixture 316 is sufficiently thick to facilitate alignment and spacing between shafts of the temperature probes and the transmission portion 315*b* of the microwave energy delivery device 515. In addition, fixture 316 facilitates spacing between the antenna portion 315*a* of the microwave energy delivery device 315 and the sensors 317*s*, 318*s*. In another embodiment, the fixture 316 includes tubes extending through the inserts thereby providing additional support for alignment of the devices 316, 317*b-e*, 318*b-e*.

Sensors 317*s*, 318*s* measure the temperature of tissue 303 spaced away from the antenna 315*a* of the microwave energy delivery device 315. Sensors 317*s*, 318*s* connect to the MRT 100 of FIG. 1 through the temperature sensor assembly connectors 317*a*, 318*a*.

An ablation algorithm, executing in the MRT 100 of FIG. 1, uses data from the testing assembly 300, and more specifically, the temperature measurements from the sensor 317*s*, 318*s*, to estimate the size of the ablation. While the ablation size for each test may be determined through manual measurements, an ablation algorithm to estimate the ablation size may be utilized.

For example, an ablation algorithm may include a testing procedure utilizing fixture 316 to accurately estimate and/or measure the ablation size. In one embodiment the ablation algorithm estimates the average diameter of an ablation region generated by the microwave energy delivery device 315 positioned in the fixture 316 and inserted into tissue 303.

Figure 4:
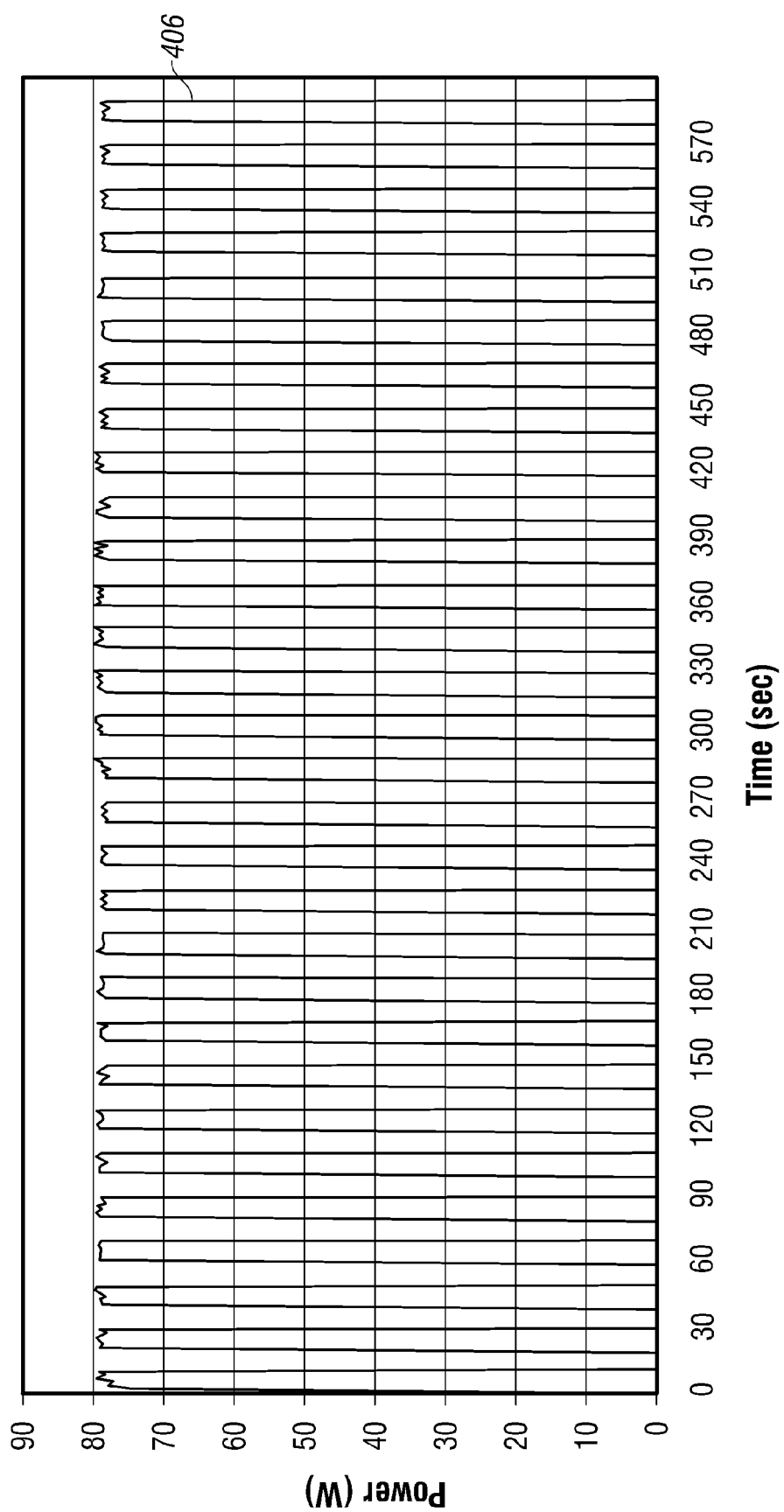
FIG. 4. is a graph of a pulsed forward power waveform generated by the microwave energy delivery, measurement and control system of FIG. 1.

The testing procedure utilizes the functionality of the MRT 100 of FIG. 1 to implement a duty-cycle and deliver a pulsed microwave energy signal to the microwave energy delivery device 115 as opposed to a continuous wave. The desired ON and OFF time of the duty cycle may be selectable via the VI interface in the user interface 175. FIG. 4 illustrates an example of a pulsed forward power signal 406 delivered to the microwave energy delivery device 115 at a 50% duty cycle.

In addition to temperature measurements, the MRT 100 of FIG. 1 periodically measures and/or records one of forward and reflected power. Using known manufacture specifications of attenuation for transmission lines (i.e., flexible cable, connectors and the transmission line in the microwave energy delivery device) the delivered energy algorithm calculates an estimation of delivered energy (i.e., the energy delivered to tissue 303 at the antenna feed point). Delivered energy may be measured by any other suitable method known in the art.

The testing procedure includes the steps of: placing the microwave energy delivery devices and temperature sensors in tissue; delivering microwave energy to tissue; measuring forward power, reflected power and temperature; terminating the delivery of microwave energy; calculating delivered power; and calculating ablation size. Delivered energy (from the delivered energy algorithm) and the ablation size (from by the ablation algorithm) may be used to compare the performance of the various types of microwave energy delivery devices.

The cooled microwave energy delivery devices may require the additional steps of connecting a peristaltic pump and setting the pump to an acceptable flow rate that provides adequate cooling.

The ablation algorithm may be periodically verified by performing the steps of: removing the microwave energy ablation device and temperature probes from the tissue after ablation is complete; administering a single cut in tissue along the same axis as the temperature probes; and verifying the ablation size by measuring the average width of the ablation area.

Testing Results

An observation of the testing was that the duty-cycling of power signal delivered to the microwave energy delivery device 115 did not provide a gain in the ablation size or provide a gain in delivered energy. For example, the ablation size generated by a continuous 27 Watt peak forward power signal was nearly identical to the ablation size generated by a 50% duty cycle 54 Watt peak forward power signal for tests with the same test duration. In addition, testing with varying duty-cycle on-off times of 5 seconds, 10 seconds, 15 seconds and 20 seconds also failed to provide a gain in ablation size for tests with the same test duration.

Another observation was that a direct correlation exists between the amount of delivered energy and the resulting ablation size for each power and duty cycle setting. For example, similar ablation sizes were achieved by delivering similar amounts of energy to tissue independent of the power setting, duty cycle or test duration.

An unexpected observation was that discrepancies in performance existed between the various types of antennas. More specifically, it was observed that the amounts of energy delivered to tissue for a given forward power varied based on the type of microwave energy delivery device. For example, 30 W delivered by a cooled microwave energy delivery device at 100% duty cycle for a test period of 10 minutes resulted in approximately 17 kJ of energy delivered to tissue and an average ablation size of 2.9 cm. In contrast, 30 W delivered by a non-cooled microwave energy delivery device at 100% duty cycle for a test period of 10 minutes resulted in approximately 14 kJ of energy delivered to tissue and an ablation size of 2.5 cm.

It was concluded that the difference is due to the overall antenna design as well as the precision of the energy calculation. For example, the non-cooled antenna includes a choke to confine energy to the tip of the antenna during ablation resulting in an increase in reflected power. As compared to the cooled microwave energy ablation device, energy radiates freely within the tissue and along the shaft. A third antenna, with both fluid cooling and an improved choke, resulted in even less energy delivered to tissue and a smaller ablation size due to both the choke and the losses in the fluid.

As a result, device specific energy algorithms were formulated to account for differences between the tested microwave energy delivery devices. The device specific energy algorithms may account for attributes (or deficiencies) of a device that result in an increase (or decrease) in ablation size, efficiencies losses due to energy absorption (i.e. absorption from cooling fluid) or any other difference that may cause discrepancies in device performance.

Device specific energy algorithms may be configured such that all devices generate a standard ablation size at a given microwave power setting. For example, the algorithm may adjust the power output, the power feedback, or any other suitable parameter such that a given power setting over a standard period of time generates the same ablation size for any microwave energy delivery device.

Device specific energy algorithms may be configured such that a microwave energy power setting on a microwave generator corresponds to energy delivered to tissue. For example, a given generator power setting over a standard period of time may correspond to a standard amount of energy delivered to tissue and near identical ablation sizes regardless of the type of microwave energy delivery device.

Microwave Generator with Enhanced Control Algorithms

Figure 5:
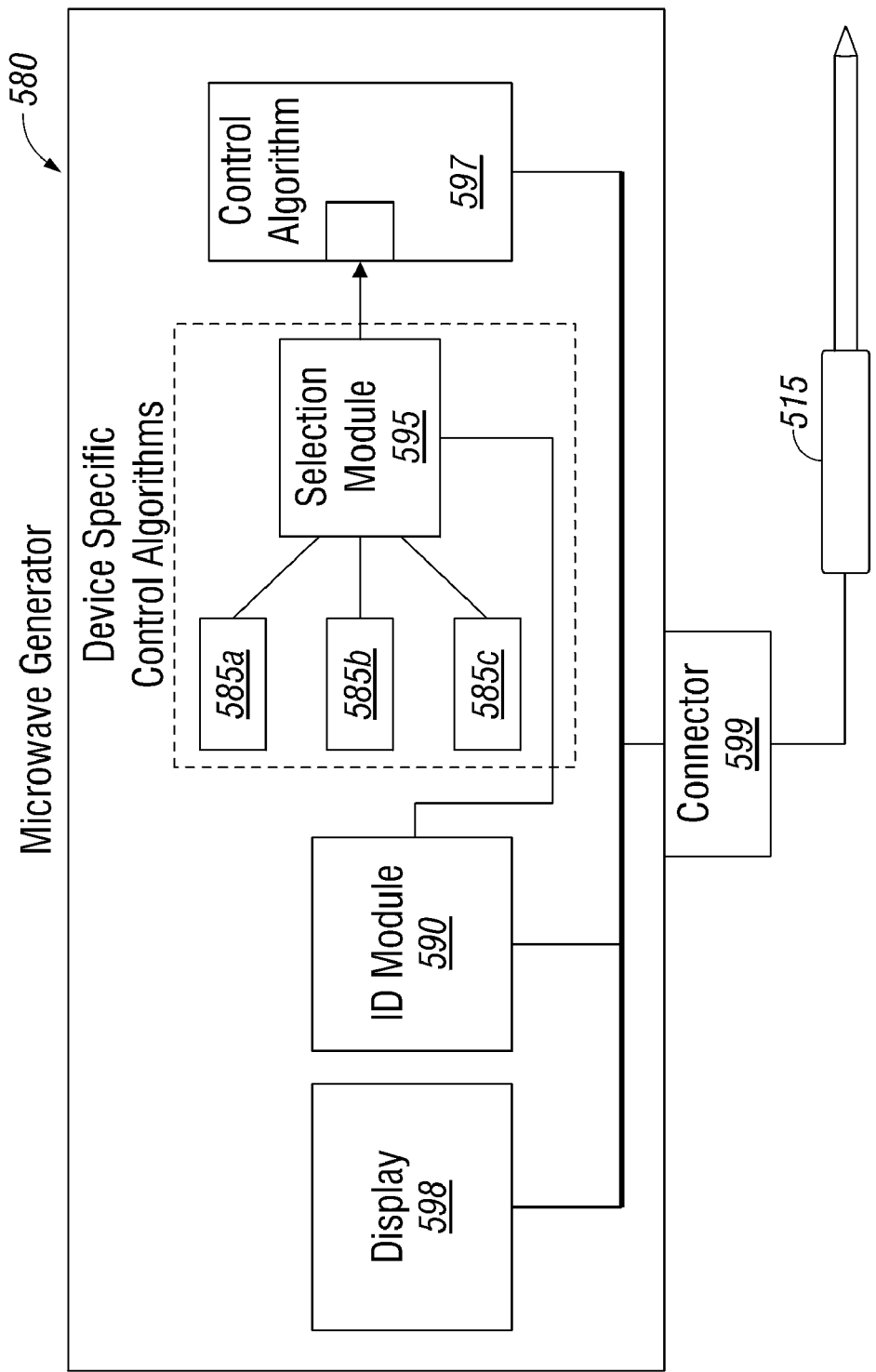
FIG. 5 is a schematic of a microwave generator in accordance with one embodiment of the present disclosure.

FIG. 5 illustrates a microwave generator 580 that includes enhanced control algorithms in accordance with one embodiment of the present disclosure. Microwave generator 580 includes at least two energy control algorithms 585a-c, wherein the microwave generator 580 is configured to select an energy control algorithm 585a that corresponds to a microwave energy delivery device 515.

In another embodiment of the present disclosure a microwave generator 580 includes a microwave energy delivery device identification module 590 and an energy control algorithm selection module 595 configured to select an device specific control algorithm 585a-c that corresponds to the identified microwave energy delivery device 515.

A microwave energy delivery device 515 containing a device specific identification characteristic as described hereinabove connects to connector 599 of the microwave generator 580. The microwave energy delivery device identification module 590 is configured to identify the identification characteristic and determine the type of microwave energy delivery device 515 connected to the connector 599. Device identification may be done actively or passively. An active method may include reading or identifying an identification characteristic on the microwave energy delivery device 515, such as, for example, a bar code, an Aztec code, an RF ID, an identification resistor, memory containing device identification information or a physical characteristic of the device 515 configured to provide identification (e.g., a key-type connector unique to the particular device). A passive method may include analyzing and identifying a forward or reflected energy identification characteristics or an impedance identification characteristic or identifying any suitable features or characteristic that identifies the device 515.

Control algorithm selection module 595 is configured to select a device specific control algorithm corresponding to the identified microwave energy delivery device 515 from two or more device specific control algorithms 585a-c. Control algorithm selection module 595 receives identification data from microwave energy delivery device identification module 590, selects a corresponding device specific control algorithm 585a-c and provides the selected device specific control algorithm 585a-c to the generator control algorithm 597.

Generator control algorithm 597 may include a default control algorithm that may be used if the identification module 590 fails to identify the microwave energy delivery device 515. Alternatively, the microwave generator 580 may use a default control algorithm to initially drive the microwave energy delivery device 515 while the identification module 590 is passively identifying the microwave energy delivery device 515.

Microwave generator 580 may further include a display 598 to provide information to the clinician. For example, display 598 may indicate one or more energy delivery parameter such as, for example, energy delivered by the microwave generator, energy reflected back to the microwave generator 580 and/or energy delivered to tissue.

Display may also provide one or more parameters related to the microwave energy delivery device 515. For example, display may provide the identification characteristic, the device model and/or type, the total energy delivered to tissue or the device efficiency. Display may be a graphical display, a text display or a combination thereof.

A method of the present disclosure may include the additional steps of: identifying a microwave energy delivery device 515 connected to a microwave generator 580; selecting an energy algorithm 585a-c that corresponds to the identified device 515 and using the selected algorithm. The method may further include the step of displaying at least one characteristic related to energy delivery or an identification characteristic of the microwave energy delivery device 515.

Another method of the present disclosure may include the steps of: delivering energy to a microwave energy delivery device 515; measuring at least one parameter related to the energy delivery; identifying the microwave energy delivery device 515 from the at least one parameter; selecting an energy algorithm 585a-c that corresponds to the identified device and using the selected algorithm.

Yet another method of the present disclosure includes the steps of: delivering a first pulse of microwave energy to a microwave energy delivery device 515 and measuring at least one parameter related to the energy delivery; identifying the microwave energy delivery device 515 from the at least one parameter; selecting an energy algorithm 585a-c that corresponds to the identified device and delivering subsequent pulses using the identified algorithm.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A microwave system, comprising:
   a microwave generator configured to generate microwave energy according to an energy control algorithm, the microwave generator being configured to select one of at least two energy control algorithms programmed in the microwave generator that corresponds to a microwave energy delivery device connected to the microwave generator; and a microwave energy delivery device identification module configured to actively identify the microwave energy delivery device connected to the microwave generator, wherein the microwave energy delivery device identification module is configured to actively identify one of a bar code, an Aztec code, an RFID tag, memory containing device identification information and a physical characteristic of the microwave energy delivery device.

2. The microwave system according to claim 1, further comprising:
an energy control algorithm selection module configured to select the energy control algorithm that corresponds to the connected microwave energy delivery device.

3. The microwave system according to claim 2 wherein the energy control algorithm is configured to select between at least two energy delivery algorithms.

4. The microwave system according to claim 1, further comprising:
an energy control algorithm selection module configured to receive data related to the identified microwave energy delivery device from the microwave energy delivery device identification module, the energy control algorithm selection module configured to select the energy control algorithm that corresponds to the identified microwave energy delivery device.

5. A method of delivering microwave energy comprising the steps of:
including an identification characteristic in a microwave energy delivery device;
identifying the identification characteristic;
selecting an energy algorithm that corresponds to the identified identification characteristic; and
using the selected energy algorithm to deliver microwave energy to tissue
wherein the identification characteristic is selected from a group consisting of a resistor circuit, a bar code, an Aztec code, an RFID tag, memory containing device identification information and a physical characteristic of the microwave energy delivery device.

6. The microwave system according to claim 1, wherein a first algorithm of the at least two energy control algorithms corresponds to a first microwave energy delivery device and a second algorithm of the at least two energy control algorithms corresponds to a second microwave energy delivery device different than the first microwave energy delivery device.

* * * * *